United States Patent [19]
Shioya et al.

[11] Patent Number: 5,089,272
[45] Date of Patent: Feb. 18, 1992

[54] PROCESS FOR PRODUCING CAPSULES HAVING A PERMEABILITY-CONTROLLABLE MEMBRANE

[75] Inventors: Toshiaki Shioya, Oume; Ryogo Hirano, Kawagoe, both of Japan

[73] Assignee: Snow Brand Milk Products Co., Ltd., Hokkaido, Japan

[21] Appl. No.: 330,845

[22] Filed: Mar. 29, 1989

[51] Int. Cl.$^5$ .................. A61K 9/62; A61K 37/00
[52] U.S. Cl. .................. 424/493; 424/494; 514/777; 514/779; 514/781; 514/963
[58] Field of Search ............ 514/777, 779, 781, 963; 424/493, 494

[56] References Cited

U.S. PATENT DOCUMENTS

| | | | |
|---|---|---|---|
| 3,567,650 | 3/1971 | Bakan | 424/494 |
| 3,594,326 | 7/1971 | Himmel | 424/494 |
| 4,016,098 | 4/1977 | Saeki et al. | 514/714 |
| 4,744,933 | 5/1988 | Rha et al. | 514/963 |
| 4,808,707 | 2/1989 | Daly et al. | 514/963 |

Primary Examiner—Ronald W. Griffin
Attorney, Agent, or Firm—Seed and Berry

[57] ABSTRACT

The present invention relates to a process for producing a microcapsule comprising a permeability-controllable membrane. This process comprises adjusting the ionic strength of a solution of a soluble chitin derivative, and then bringing this solution into contact with a solution of a polyanionic polysaccharide, its salt or a mixture thereof.

9 Claims, 3 Drawing Sheets

PROCESS FOR PRODUCING CAPSULES HAVING A PERMEABILITY-CONTROLLABLE MEMBRANE

BACKGROUND OF THE INVENTION

1. Field of the Invention

The present invention relates to a process for producing capsules having a permeability-controllable membrane by using a soluble chitin derivative such as chitosan as a membrane-forming material.

2. Prior Art

In the biotechnologic field, much attention has been paid to a micro-capsulation process wherein a microorganism or an enzyme is immobilized with capsules or wherein animal cells are cultured in capsules.

In the micro-capsulation process, the cells can be protected from a mechanical shearing force during the culture. Also, the permeability of the capsule membrane is controllable. Therefore, physiologically active substances produced by the cells can be accumulated at a high concentration in the capsules and the substances can be recovered in an advantageous manner. In addition, by this micro-capsulation process, the cells can be easily separated from the culture solution.

However, in the micro-capsulation process, the permeability of the capsule membrane cannot be easily controlled at a certain level. In order to resolve this problem, there has been proposed, as disclosed in Japanese Patent Unexamined Published Application (hereinafter referred to as 'J.P. KOKAI') No. 55-44387, a process for producing semipermeable microcapsules, wherein the permeability of the microcapsule membrane is controlled by adjusting a parameter in interfacial polymerization reaction during the formation of the membrane. However, this process is yet impractical, because its process is complicated and various solvents are necessitated.

SUMMARY OF THE INVENTION

An object of the present invention is, therefore, to provide a process for producing capsules having a membrane, the permeability of which can be controlled precisely at will in an easy manner.

After intensive investigations made for the purpose of attaining the above-described object, the inventors have found out that by adjusting the ionic strength of a solution used for forming the capsules before the production of the capsules, those capsules having a membrane, the permeability of which corresponds to the adjusted ionic strength, can be produced. The present invention has been completed on the basis of this finding.

The present invention relates to a process for producing capsules comprising bringing a solution of a polyanionic polysaccharide, its salt or a mixture thereof, into contact with a solution of a soluble chitin derivative, to form capsules comprising the former solution as a core, wherein the ionic strength of the solution of a soluble chitin derivative is adjusted before the former solution is brought into contact with the solution of a soluble chitin derivative.

DETAILED DESCRIPTION OF THE INVENTION

Figure 1:
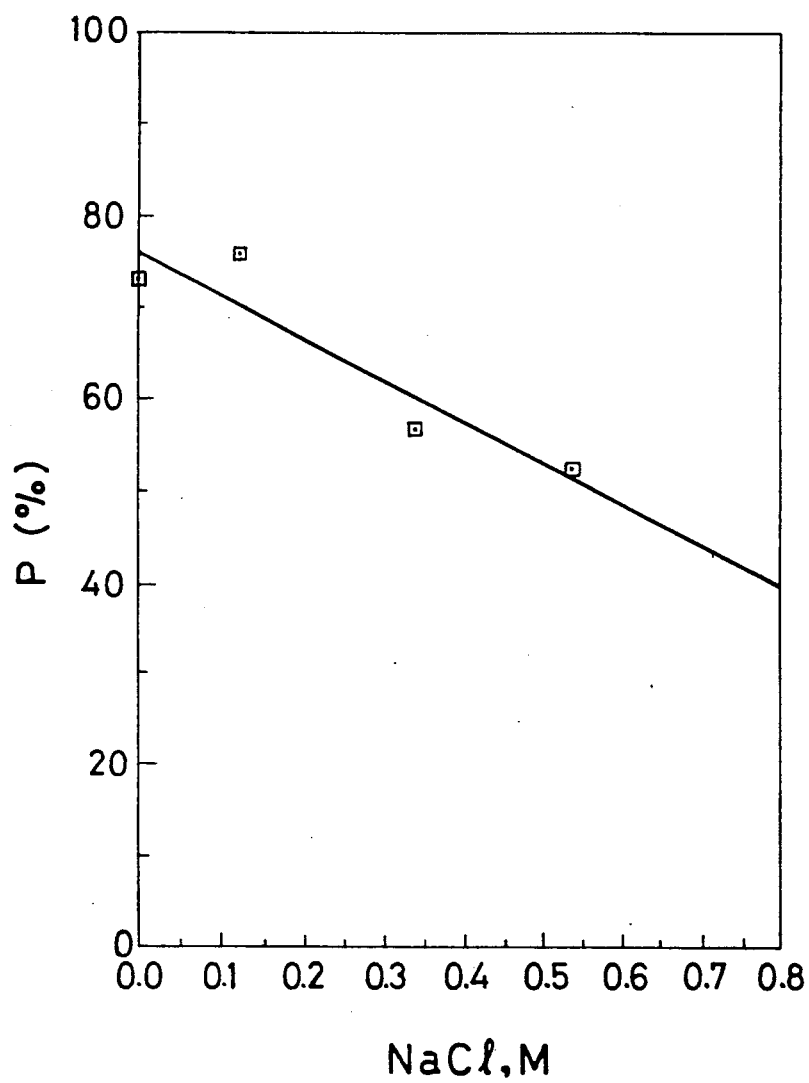
FIGS. 1 and 2 show the relationship between the permeability of the capsule membrane and the ionic strength.

The polyanionic polysaccharide or its salt usable for forming the gel membrane of the capsules in the present invention is a polysaccharide capable of forming a polyanionic polymer or its salt. Such a polysaccharide includes, for example, a low methoxylpectin (having a low methoxyl group content), carrageenan, carboxymethyl cellulose, sodium alginate and chondroitin sulfate. The polysaccharide can be used either singly or as a mixture of the polysaccharides. The molecular weight of the polysaccharide is preferably $10^4$ to $10^6$ from the viewpoint of the capsule-forming capacity.

The soluble chitin derivative usable for forming the gel membrane is produced by chemically treating essentially inert chitin, to enhance its reactivity. A typical example of the chitin derivatives is chitosan, which is formed by deacetylating chitin.

Chitin is a straight chain homopolysaccharide comprising N-acetyl-D-glucosamine molecules bonded through $\beta(1\rightarrow4)$ bond. It is contained in shells of crabs, krills and insects, cell walls of microorganisms, and fungi. Although chitin is naturally generated in a large quantity, it is unusable as it is, because it is inert. Chitin is, therefore, one of unused natural resources.

Chitin derivatives such as chitosan produced by deacetylating chitin are soluble in a dilute acid and have a reactivity. Namely, chitosan comprises a structural unit having the following general formula (I):

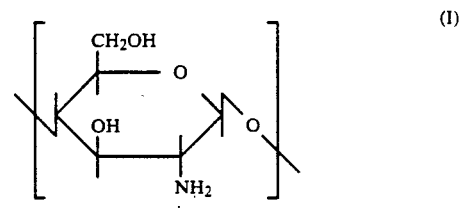

(I)

Chitosan is positively charged due to the amino group shown in the above formula and is reactive as a polycationic polymer.

The molecular weight of the chitin derivative is preferably $10^5$ to $10^6$ from the viewpoint of the capsule-forming capacity.

When a solution of chitosan (a soluble chitin derivative as described above) is brought into contact with an aqueous solution of the above-described polyanionic polysaccharide, its salt or a mixture thereof, crosslinking due to the charge occurs between the polyanionic polysaccharide and chitosan, to form crosslinkage and form a gel substance.

These two solutions can be brought into contact with each other by dropwise adding an aqueous solution of the polyanionic polysaccharide or its salt to the chitosan solution by means of a depositor or the like under stirring. By this contact, the crosslinking starts. Once the gel membrane is formed by the crosslinkage, the solution constituting the core inside the membrane (core solution) is not gelatinized at all and, therefore, the intended capsules are obtained. Supposedly, such a phenomenon occurs because, after the gel membrane is formed, the chitosan molecules can no more pass through the membrane and, consequently, the crosslinking no more proceeds in the core solution.

The solution usable as a core solution in the present invention is an aqueous solution containing 0.3 to 1.0 wt.% of the polyanionic polysaccharide, its salt or a mixture thereof and having an adjusted ionic strength. When the concentration is less than 0.3 wt.%, the capsule formation becomes difficult. On the other hand, when it exceeds 1.0 wt.%, the drop formation becomes difficult. It is preferable that the gel membrane is formed using carboxymethyl cellulose as the polyanionic polysaccharide.

The chitosan solution to be brought into contact with the aqueous solution is preferably a 0.5 to 1.0 wt.% solution of chitosan in a weak acid such as acetic acid or glutamic acid. When the concentration is less than 0.5 wt.%, the membrane formation becomes difficult. On the other hand, when it exceeds 1.0 wt.%, the introduction of the core solution into the chitosan solution becomes difficult.

The ionic strength of the solution of the soluble chitin derivative can be adjusted by, for example, placing the solution in a dialysis tube and then conducting the dialysis with pure water. By this dialysis, most part of free ions can be removed. By adding a suitable amount of a neutral salt such as a neutral salt of hydrohalogenic acid, for example, sodium chloride, potassium chloride, lithium chloride, and a neutral salt of phosphoric acid to the solution of the soluble chitin derivative from which the free ions have been removed, the solution having a desired ionic strength is easily obtained. The capsules prepared from the solution having a low ionic strength have a dense membrane structure and their capsule membrane has a low permeability. As the ionic strength is increased, the permeability of the capsule membrane is increased.

According to the present invention, the gel membrane of the capsule can be formed without necessitating an organic solvent under quite mild conditions, namely, under mild biological conditions in a short time. Therefore, unstable biological substances, functional substances and various other additives suitable for the use of the capsule can be dispersed in the core solution. Thus, the capsules containing various useful substances in its core solution can be provided.

The present process which is capable of forming capsules by forming the gel membranes in one step, is more advantageous than known capsule formation processes such as a process disclosed in J.P. KOKAI No. 57-197031 wherein the capsules are formed using salt crosslinkage between a polyanion and a polycation.

The permeability of the capsule membrane can be easily adjusted by controlling the gel membrane-forming conditions according to the present invention and, therefore, the capsule, the membrane of which has a fractionating function, can be produced.

As described above, the present invention is advantageous in that the capsules usable for a wide range of purposes can be produced from easily available starting materials by simple process in a short time.

The following examples will further illustrate the present invention.

EXAMPLE 1

Two solutions were prepared from CMC (carboxymethyl cellulose) having a molecular weight of $2.6 \times 10^5$ and chitosan having a molecular weight of $2.8 \times 10^6$. These solutions were dialyzed against pure water for two days. Serum albumin having a molecular weight of about 70,000 was added to the CMC solution as a protein and the mixture was used as a core solution for the capsules. The final CMC concentration was 0.5%. 0.1 to 0.7 M of sodium chloride was added to the chitosan solution in order to adjust the ionic strength so as to form the chitosan solutions having various ionic strengths.

Capsules were prepared from these solutions. The protein concentrations inside and outside the resultant capsules were measured over the lapse of time. The permeability of the capsule membrane was determined according to the following formula:

$$P(\%) = \frac{CiVi}{CiVi + CoVo} \times 100$$

wherein

Ci represents the protein concentration inside the capsule,

Vi represents the total volume of the capsule,

Co represents the protein concentration outside the capsule, and

Vo represents the volume of the liquid in which the capsule is placed.

The results are shown in FIG. 1. It is apparent from FIG. 1 that as the ionic strength is increased, the permeability of the capsule membrane is increased and the protein concentration (P) is reduced Namely, the higher the ionic strength, the easier it is for the protein to pass through the capsule membrane.

This fact indicates that the permeability of the capsule membrane can be easily controlled by adjusting the ionic strength.

EXAMPLE 2

Figure 2:
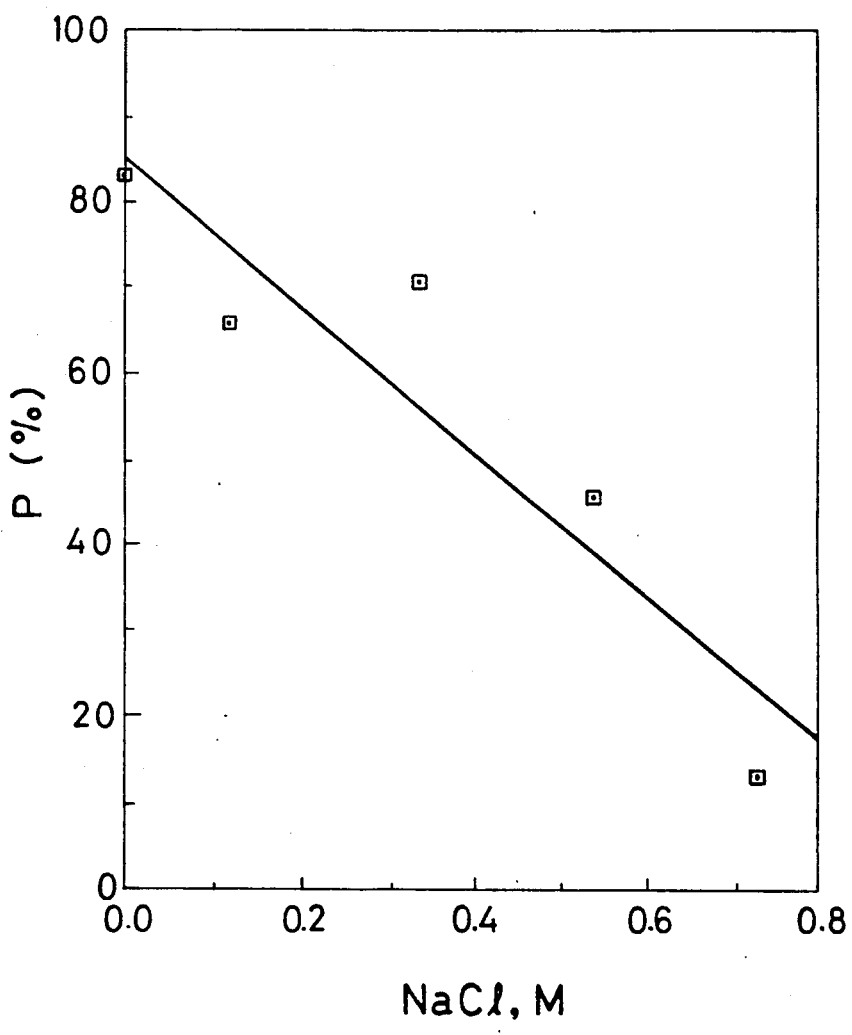

The same procedure as that of Example 1 was repeated except that chitosan having a molecular weight of $1.6 \times 10^6$ was used. The results are shown in FIG. 2.

The results were similar to those obtained for Example 1.

EXAMPLE 3

The present invention was applied to the cell culture.

A dispersion of animal cells (hybridoma) capable of producing an immunoprotein (IgG) in a 0.5% CMC solution was prepared as a core solution.

(1) a dialyzed chitosan solution, and (2) a mixture of the dialyzed chitosan solution with a 1% sodium chloride were prepared. Capsules were prepared from these solutions.

The capsules were cultured in a serum-free culture medium for 11 days. During the culture, the IgG concentrations inside and outside the capsules were measured. The amount of IgG contained in the capsules was determined according to the following formula:

$$\text{IgG retention} \atop (\%) = \frac{(\text{IgG inside capsule}) \times 100}{(\text{IgG inside capsule}) + (\text{IgG outside capsule})}$$

Figure 3:
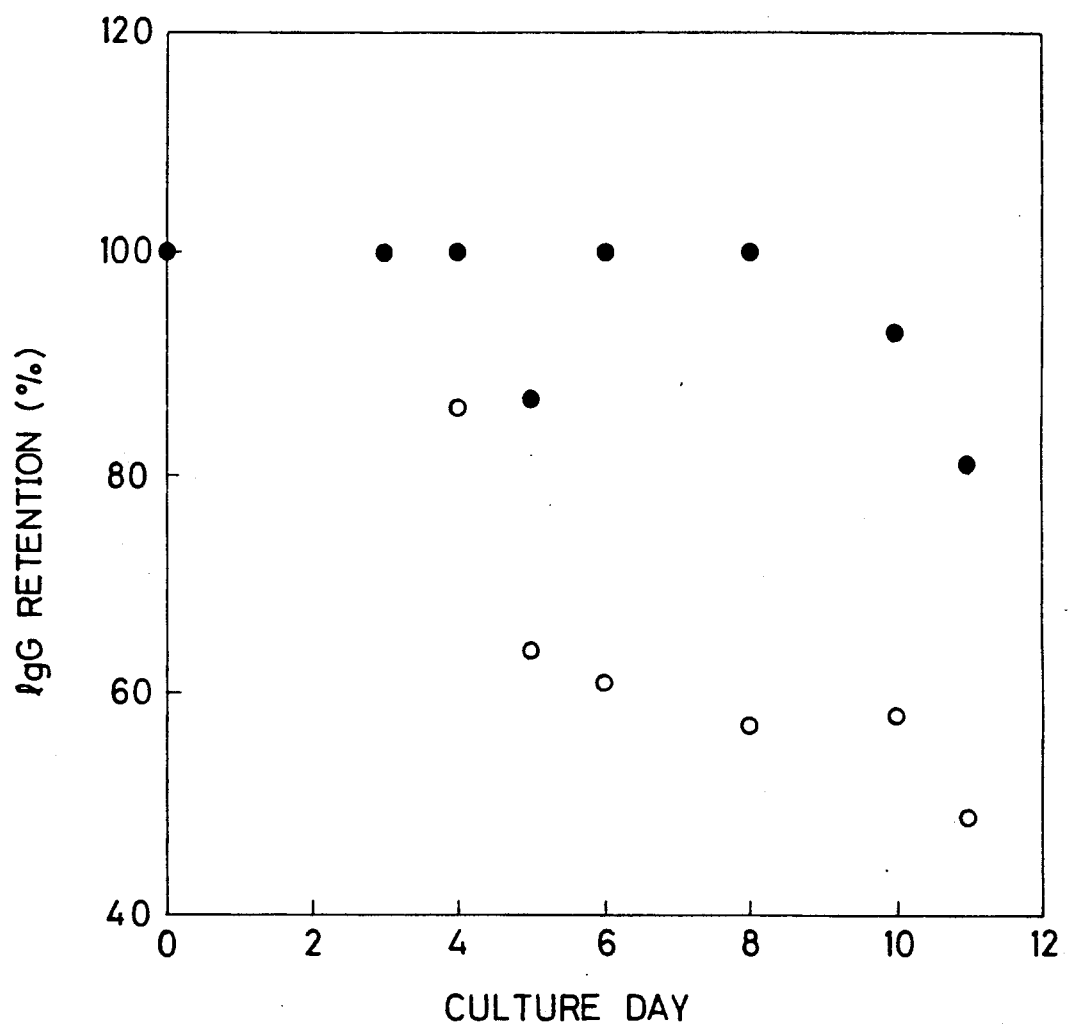
FIG. 3 shows the results of the determination of the permeability of the membrane to immunoprotein produced from hybridoma culture.

The results are shown in FIG. 3.

In FIG. 3, the results obtained by using the dialyzed chitosan solution (1) are shown by black dots and those obtained by using the mixture (2) of the chitosan solution with a 1% sodium chloride are shown by white dots.

IgG scarcely leaked out of the capsule prepared from the dialyzed chitosan (1) and was kept inside the capsule. However, IgG leaked out of the capsule prepared from the sodium chloride-containing chitosan solution (2).

As described above, by adjusting the ionic strength of the chitosan solution, IgG can be accumulated at a high concentration inside the capsule, or it can be passed through the membrane to the outside. Namely, the permeability of the capsule membrane can be easily controlled.

What is claimed is:

1. A process for producing a capsule containing, as a core, a solution (a) of a polyanionic polysaccharide, its salt or a mixture thereof and having a permeability-controllable membrane, said process comprising:

preparing a solution (b) of chitosan;
dialysing the solution (b);
adjusting the ionic strength of the solution (b); and then
bringing the solution (a) into contact with the solution (b).

2. The process of claim 1, wherein said polyanionic polysaccharide or its salt is selected from the group consisting of a lower methoxylpectin, carrageenan, carboxymethyl cellulose, sodium alginate and condroitin sulfate.

3. The process of claim 1, wherein said polyanionic polysaccharide or its salt has a molecular weight of $10^4$–$10^6$.

4. The process of claim 1, wherein the chitosan has a molecular weight of $10^5$–$10^6$.

5. The process of claim 1, wherein said ionic strength of said solution (b) is adjusted by adding a salt to the solution (b).

6. The process of claim 5, wherein said salt is a neutral salt.

7. The process of claim 6, wherein said neutral salt is selected from the group consisting of sodium chloride, potassium chloride and lithium chloride.

8. The process of claim 1, wherein the concentration of the solution (a) is 0.3 to 1.0 wt. %.

9. The process of claim 1, wherein the concentration of the solution (b) is 0.5 to 1.0 wt. %.

* * * * *